United States Patent
Macharia et al.

(10) Patent No.: US 8,634,940 B2
(45) Date of Patent: Jan. 21, 2014

(54) MODEL PREDICTIVE CONTROL OF A FERMENTATION FEED IN BIOFUEL PRODUCTION

(75) Inventors: Maina A. Macharia, Round Rock, TX (US); Patrick D. Noll, Richardson, TX (US); Michael E. Tay, Georgetown, TX (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 1217 days.

(21) Appl. No.: 11/757,557

(22) Filed: Jun. 4, 2007

(65) Prior Publication Data

US 2008/0104003 A1   May 1, 2008

Related U.S. Application Data

(60) Provisional application No. 60/863,759, filed on Oct. 31, 2006.

(51) Int. Cl.
*C12M 1/38* (2006.01)
*G05B 13/04* (2006.01)

(52) U.S. Cl.
USPC ............ 700/29; 700/28; 700/33; 700/36; 700/44; 700/51; 703/11

(58) Field of Classification Search
CPC ...... C12M 41/30; C12M 41/32; C12M 41/48; C12M 45/02; G05D 7/06
See application file for complete search history.

(56) References Cited

U.S. PATENT DOCUMENTS

| | | | |
|---|---|---|---|
| 3,219,319 A * | 11/1965 | Ash ........................ | 435/286.5 |
| 4,309,254 A | 1/1982 | Dahlstrom et al. | |
| 4,626,321 A | 12/1986 | Grethlein et al. | |
| 4,874,134 A * | 10/1989 | Wiens ........................ | 241/19 |
| 5,177,008 A | 1/1993 | Kampen | |
| 5,407,817 A | 4/1995 | Lightsey et al. | |

(Continued)

FOREIGN PATENT DOCUMENTS

| WO | WO 2005113104 A1 * | 12/2005 | ............ B01D 17/12 |
|---|---|---|---|
| WO | WO 2006/016889 | * 2/2006 | ............ G05B 21/00 |

OTHER PUBLICATIONS

Grosman, B. & Lewin, D. R. Automated nonlinear model predictive control using genetic programming. Computers & Chemical Engineering 26, 631-640 (2002).*

(Continued)

*Primary Examiner* — Soren Harward
(74) *Attorney, Agent, or Firm* — Fletcher Yoder P.C.; William R. Walburn; John M. Miller

(57) ABSTRACT

System and method for managing fermentation feed in a biofuel production process, comprising a dynamic multivariate predictive model-based controller coupled to a dynamic multivariate predictive model. The model is executable to: receive process information, including water inventory and biomass information, from the biofuel production process; receive a specified objective for the fermentation feed specifying a target biomass concentration; and generate model output comprising target values for a plurality of manipulated variables of the biofuel production process, including target flow rates of water and/or biomass contributing to the fermentation feed in accordance with the specified objective. The controller is operable to dynamically control the biofuel production process by adjusting the plurality of manipulated variables to model-determined target values to stabilize water/biomass balance in the fermentation feed in accordance with the specified objective, including the specified target biomass concentration.

30 Claims, 6 Drawing Sheets

(56) References Cited

U.S. PATENT DOCUMENTS

| | | | |
|---|---|---|---|
| 5,477,444 | A | 12/1995 | Bhat et al. |
| 5,874,263 | A * | 2/1999 | Holtzapple et al. ......... 435/289.1 |
| 5,893,523 | A * | 4/1999 | Irwin ............................. 241/60 |
| 5,932,456 | A | 8/1999 | Van Draanen et al. |
| 6,284,453 | B1 * | 9/2001 | Siano ............................... 435/3 |
| 6,510,368 | B1 | 1/2003 | Beardwood et al. |
| 6,609,119 | B1 | 8/2003 | Meghlaoui |
| 6,792,336 | B1 | 9/2004 | Johnson et al. |
| 6,799,883 | B1 * | 10/2004 | Urquhart et al. ........... 366/152.4 |
| 6,934,931 | B2 | 8/2005 | Plumer et al. |
| 6,955,892 | B2 * | 10/2005 | Lin et al. ......................... 435/41 |
| 7,096,093 | B1 * | 8/2006 | Hansen et al. ................ 700/282 |
| 2002/0077711 | A1 | 6/2002 | Nixon et al. |
| 2002/0138454 | A1 * | 9/2002 | Gruenberg et al. ............... 706/7 |
| 2003/0040642 | A1 | 2/2003 | Goto et al. |
| 2004/0023349 | A1 | 2/2004 | Bisgaard-Frantzen et al. |
| 2004/0030516 | A1 * | 2/2004 | Dunhill et al. .................. 702/83 |
| 2004/0049299 | A1 * | 3/2004 | Wojsznis et al. ................ 700/29 |
| 2004/0091954 | A1 * | 5/2004 | Lin et al. ......................... 435/41 |
| 2005/0112739 | A1 | 5/2005 | Golubkov |
| 2005/0233030 | A1 | 10/2005 | Lewis et al. |
| 2006/0216818 | A1 * | 9/2006 | Amano ...................... 435/287.5 |
| 2006/0225350 | A1 | 10/2006 | Spallone et al. |
| 2007/0078530 | A1 | 4/2007 | Blevins et al. |
| 2007/0089356 | A1 | 4/2007 | Krasutsky et al. |
| 2008/0103747 | A1 | 5/2008 | Macharia et al. |
| 2008/0103748 | A1 | 5/2008 | Axelrud et al. |
| 2008/0108048 | A1 | 5/2008 | Bartee et al. |
| 2008/0109100 | A1 | 5/2008 | Macharia et al. |
| 2008/0109200 | A1 | 5/2008 | Bartee et al. |
| 2008/0167852 | A1 | 7/2008 | Bartee et al. |

OTHER PUBLICATIONS

Kleman, G. L., Chalmers, J. J., Luli, G. W. & Strohl, W. R. A predictive and feedback control algorithm maintains a constant glucose concentration in fed-batch fermentations. Appl. Environ. Microbiol. 57, 910-917 (1991).*

Marjanovic, O., Lennox, B., Sandoz, D., Smith, K. & Crofts, M. Real-time monitoring of an industrial batch process. Computers & Chemical Engineering 30, 1476-1481 (2006).*

Qin, S. J. & Badgwell, T. A. A survey of industrial model predictive control technology. Control Engineering Practice 11, 733-764 (2003).*

Zhang, H. & Lennox, B. Integrated condition monitoring and control of fed-batch fermentation processes. Journal of Process Control 14, 41-50 (2004).*

Lennox, B., Montague, G. A., Hiden, H. G., Kornfeld, G. & Goulding, P. R. Process monitoring of an industrial fed-batch fermentation. Biotechnology and Bioengineering 74, 125-135 (2001).*

Henson, M.; "Nonlinear model predictive control: current status and future directions," Computers & Chemical Engineering, vol. 23, pp. 187-202 (1998).

Grosman, B. & Lewin, D.R.; "Automated nonlinear model predictive control using genetic programming," Computers & Chemical Engineering, vol. 26, pp. 631-640 (2002).

S. Piche, et al.; "Nonlinear model predictive control using neural networks," Control Systems Magazine, IEEE, vol. 20, pp. 53-62 (2002).

Q. Miao, et al.; "Nonlinear model predictive control based on support vector regression," 2002 International Conference on Machine Learning and Cybernetics, vol. 3, pp. 1657-1661 (2003).

S. Qin; "A survey of industrial model predictive control technology," Control Engineering Practice, vol. 11, pp. 733-764 (2003).

B. Kamm et al.; "Principles of biorefineries," Applied Microbiology and Biotechnology, vol. 64, pp. 137-145 (2004).

T. Raiko, et al.; "Learning nonlinear state-space models for control," In Proceedings, 2005 IEEE International Joint Conference on Neural Networks, 2005, IJCNN '05, vol. 2, pp. 815-820 (2005).

Van Gerpen J et al., Biodiesel Production Technology: Aug. 2002-Jan. 2004, National Renewable Energy Laboratory Report No. SR-510-36244, [Online] Jul. 2004, pp. 1-110, XP002483519 Retrieved from the Internet: http://www.nrel.gov/docs/fy04osti/36244.pdf.

Zhang Y et al., Biodiesel Production from Waste Cooking Oil: 1. Process Design and Technological Assessment, Bioresource Technology, Elsevier, GB, vol. 89, No. 1, Jan. 1, 2003, pp. 1-16, XP003001656, ISSN:0960-8524, pp. 4, figure 2.

De Filippis P et al., Transesterification Processes for Vegetable Oils: A Simple Control Method of Methyl Ester Content, Journal of the American Oil Chemists' Society, Springer, vol. 72, No. 11, Nov. 1999, pp. 1399-1404, XP002475271, Berlin/Heidelberg, ISSN:0003-021X.

Zagonel G F et al., Multivariate Monitoring of Soybean Oil Ethanolysis by FTIR, Talanta, vol. 63, No. 4, Jul. 8, 2004, pp. 1021-1025, XP002475272, ISSN:0039-9140.

Ghesti G F et al., Application of Raman Spectroscopy to Monitor and Quantify Ethyl Esters in Soybean Oil Transesterification, Journal of the American Oil Chemists' Society, vol. 83, No. 7, Jul. 2006, pp. 597-601, XP002475273, Berlin/Heidelberg, ISSN:0003-021X.

De Andres-Toro, B., et al., "Evolutionary Optimization of an Industrial Batch Fermentation Process", European Control Conference, 1997, http://www.cds.caltech.edu/conferences/related/ECC97/proceeds/501_750/ECC615.PDF, 6 pages.

De Andres-Toro, B, J.M Giron-Sierra, J.A. Lopez-Orozco, C. Ferandez-Conde, "Application of genetic algorithms and simulations for the optimization of batch fermentation control", Systems, Man, and Cybernetics, 1997. 'Computational Cybernetics and Simulation'., 1997 IEEE International Conference on Oct. 12-15, 1997, vol. 1, pp. 392-397.

Madar, Janos, Janos Abonyi, Balaz Balasko, Ferenc Szeifert, "Interactive Evolutionary Computation for Model Based Optimization of Batch Fermentation", European Control Conference, 1997, 6 pages.

U.S. Appl. No. 12/052,117, filed Mar. 20, 2008, Stephenson et al.
U.S. Appl. No. 12/052,159, filed Mar. 20, 2008, Stephenson et al.
U.S. Appl. No. 12/165,371, filed Jun. 30, 2008, Macharia et al.
U.S. Appl. No. 12/242,531, filed Sep. 30, 2008, Macharia et al.
U.S. Appl. No. 12/242,568, filed Sep. 30, 2008, Macharia et al.
U.S. Appl. No. 12/242,606, filed Sep. 30, 2008, Macharia et al.
U.S. Appl. No. 12/242,635, filed Sep. 30, 2008, Macharia et al.

* cited by examiner

```
Process          →  Dynamic                       Model                Dynamic                      Controller
Information         Multivariate                  Output               Multivariate                 Output
for                 Predictive Model of           for                  Predictive         →         for
Milling/            Biomass Concentration and     Milling/       →     Model-based                  Milling/
Cooking             Water Inventory for           Cooking              Controller                   Cooking
Process             a Fermentation Feed from                           704                          Process
                    a Milling/Cooking Process     Process
                    702

↑
             Specified Objective
             for Milling/Cooking Process
```

FIG. 7

MODEL PREDICTIVE CONTROL OF A FERMENTATION FEED IN BIOFUEL PRODUCTION

PRIORITY DATA

This application claims benefit of priority of U.S. provisional application Ser. No. 60/863,759 titled "Model Predictive Control of a Biofuel Production Process" filed Oct. 31, 2006, whose inventors were Michael E. Tay, Maina A. Macharia, Celso Axelrud, and James Bartee.

FIELD OF THE INVENTION

The present invention generally relates to the field of model predictive control of production processes for biofuel and its co-products. More particularly, the present invention relates to systems and methods for model predictive control of fermentation feed in a biofuel production process.

DESCRIPTION OF THE RELATED ART

History of Biofuel

Biofuel refers to any fuel derived from biomass, i.e., from recently living organisms or their bi-products. Biofuels were used in automobiles from approximately 1876-1908. The Otto Cycle (1876) was the first combustion engine designed to use alcohol and gasoline. Henry Ford's Model T (1908) was designed to use biofuel, gasoline, or any combination of the two fuels. However, high government tariffs on alcohol discouraged the use of biofuel, and gasoline became the predominant fuel choice for automobiles for many decades.

The energy crisis of the 1970s renewed the search for an alternative to fossil fuels. The Energy Tax Act of 1978 (H.R. 5263) provided a 4 cents per gallon exemption from Federal excise taxes to motor fuels blended with biofuel (minimum 10 percent biofuel) and granted a 10% energy investment tax credit for biomass-biofuel conversion equipment (in addition to the 10% investment tax credit available) that encouraged plant building. However, by 1985, only 45% of the 163 existing commercial biofuel plants were operational. This high plant failure rate was partially the result of poor business judgment and inefficient engineering design. In 1988, biofuel was used as an oxygenate in Denver, Colo., which mandated the use of oxygenated fuels during winter use. Oxygenated fuels are fuels that have been infused with oxygen to reduce carbon monoxide emissions and NOx emissions created during the burning of the fuel. The Clean Air Act in the 1990s, motivated an additional increase in the use of biofuel as a pollution control additive.

The US Congress passed the Clean Air Act Amendments of 1990, which mandated the use of "reformulated gasoline" containing oxygenates in high-pollution areas. Starting in 1992, Methyl Tertiary Butyl Ether (MTBE) was added to gasoline in higher concentrations in accordance with the Clean Air Act Amendments. Improvements in air quality in many areas has been attributed to the use of gas reformulated with MBTE. However by 2000, MTBE—(a known carcinogenic agent) was found to have contaminated groundwater systems, mostly through leaks in underground gasoline storage tanks. In 2004, California and New York banned MTBE, generally replacing it with ethanol. Several other states started switching soon afterward. The 2005 Energy Bill required a phase out of MTBE and did not provide legal protection for the oil companies. As a result, the oil companies began to replace MTBE with ethanol (one embodiment of a biofuel), thereby spurring growth in the biofuels industry.

Since 2001, there has been a steady rise in crude oil prices that has increased the price of gasoline above the break-even point of biofuel's cost of production. This has been very beneficial to Mid-west agricultural regions that have always sought ways to diversify demand for agricultural goods and services. Biofuel plants that had depended on subsidies to be profitable are now transitioning to an economically viable venture for this corn-rich region.

Biofuel Production Plants

An exemplary high-level design of a biofuel production plant or process is shown in FIG. 1, which illustrates how biomass is processed through several stages to produce biofuel and one or more co-products. Biomass is first provided to a milling and cooking process, e.g., milling and cooking units 104, where water 102 (and possibly recycled water RW1 and RW2) is added and the biomass is broken down to increase the surface area to volume ratio. This increase in surface area allows for sufficient interaction of the water and biomass surface area to achieve a solution of fermentable sugars in water. The mixture, a biomass and water slurry, is cooked to promote an increase in the amount of contact between the biomass and water in solution and to increase the separation of carbohydrate biomass from the non-carbohydrate biomass. The output of the milling and cooking units 104 (i.e., the fermentation feed or slurry) is then sent to a fermentation process, where one or more fermentation units 106 operate to ferment the biomass/water slurry produced by the milling and cooking process.

As FIG. 1 indicates, the fermentation process may require additional water 102 to control the consistency of material to the fermentation units (also referred to herein as a fermenter). Biomass is converted by yeast and enzymes into a biofuel and by-products such as carbon dioxide, water and non-fermentable biomass (solids), in the fermentation units 106.

The output from the fermentation units 106 is sent to a distillation process, e.g., one or more distillation units 108, to separate biofuel from water, carbon dioxide, and non-fermentable solids. If the biofuel has to be dehydrated to moisture levels less than 5% by volume, the biofuel can be processed through a processing unit called a molecular sieve or similar processing units. The finalized biofuel is then processed to ensure it is denatured and not used for human-consumption.

The distillation units 108 separate the biofuel from water. Water 102 is used in the form of steam for heat and separation, and the condensed water is recycled (RW1) back to the milling and cooking units 104, as shown in FIG. 1. Stillage (non-fermentable solids and yeast residue), the heaviest output of the distillation units, is sent to stillage processing for further development of co-products from the biofuel production process.

Stillage processing units 110 separate additional water from the cake solids and recycle this water (RW2) back to the milling and cooking units 104. There are a number of stillage processing options: stillage can be sold with minimal processing, or further processed by separating moisture from the solids product via one or more centrifuge units. From the centrifuge, the non-fermentable solids may be transported to dryers for further moisture removal. A portion of the stillage liquid (centrate) may be recycled back to the fermentation units 106; however, the bulk of the flow is generally sent to evaporator units, where more liquid is separated form the liquid stream, causing the liquid stream to concentrate into syrup, while solid stillage is sent to an evaporation process, e.g., using a drying unit or evaporator, to dry the solid stillage to a specified water content. The syrup is then sent to the syrup tank. Syrup in inventory can be processed/utilized with a number of options: it can be sprayed in dryers to achieve a specified color or moisture content; it can be added to the partially dried stillage product, or it can be is sold as a separate liquid product. The evaporator unit may have a water byproduct stream that is recycled back to the front end (RW2), e.g., to the milling and cooking units 104.

Note that an energy center 112 supplies energy to various of the processing units, e.g., the milling and cooking units 104, the distillation 108 and mole-sieve units, and the stillage processing units. The energy center 112 may constitute a thermal oxidizer unit & heat recovery steam generator that destroys volatile organic compounds (VOCs) and provides steam to the evaporators, distillation units 108, cooking system units (e.g., in 104), and dehydration units. The energy center 112 is typically the largest source of heat in the biofuels plant In prior art biofuel plants, properties such as temperature or product quality are controlled with control systems utilizing traditional control schemes.

Systems can be open or closed. An open loop system is a system that responds to an input, but the system is not modified because of the behavior of the output. FIG. 2 illustrates a generic open loop process/system 202, where the process/system 202 receives process input, and generates process output, with no feedback from output back to input. Open loop systems are only defined by the inputs and the inherent characteristics of the system or process. In the biofuel production process, the system may comprise the entire bio-processing plant, one process section of the bio-processing plant, such as the milling and cooking units, or a controller for a variable in a process such as the temperature of the cooking units.

In a closed loop system, the inputs are adjusted to compensate for changes in the output, where, for example, these changes may be a deviation from the desired or targeted measurements. The closed loop system senses the change and provides a feedback signal to the process input. FIG. 3 illustrates a generic closed loop process/system where the process/system 202 receives process input and generates process output, but where at least a portion of the output is provided back to the input as feedback. Process units in the biofuel system may be closed loop systems if they need to be regulated subject to constraints such as product quality, energy costs, or process unit capacity.

Modern plants apply traditional and advanced controls to regulate complex processes to achieve a specific control objective. Traditional PID controllers and other control systems such as ratio controls, feed-forward controls, and process models may be used to control biofuel production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

Most biofuel production facilities mill or steep corn, other grains, or other biomass (e.g. sugarcane), and mix this milled carbohydrate base with water from a variety of sources and quality.

The operating challenge is to provide a steady quality and concentration of feed to the fermentation units. However, due to variability in feed amount, flow rates, mill rates, steep efficiencies, or biomass (e.g., grain) quality, the fermentation output varies dramatically and the process operates sub-optimally due to this large variability. Fermentation end concentrations of biofuel may vary plus or minus 10% or more.

Plants are currently implemented to provide some information to plant operators to enable them to increase or decrease the feed of fermentable sugar and starch concentrations to fermentation tanks. Plant operators monitor the target feed quality and percent solids in the fermentation feed and run the plants to achieve a target percent solids so that each fermentation batch is started with a rough approximation of the target percent solids and each fermentation process runs over a specific time period in an attempt to achieve an output with approximately the design target percent of biofuel. In addition, a recycle flow rate is typically managed to maintain tank inventory levels within safe operating limits, while providing sufficient water/liquid to mix with grain or other biomass solids to fill a fermentation tank within a targeted time period (i.e. fill a vessel of 180,000 gallons in 15 hours so that the fill rate would be 600 gallons per minute).

In addition, levels of various water sources tend to increase or decrease, and operators or level controllers may adjust flows to regain targeted levels. In general, these applications are controlled with flow, level or mill speed controllers (e.g., regulatory level controllers). Some applications of ratio controllers are used in current control systems (e.g., to monitor the ratio of enzyme flow rates to grain slurry flow rates).

Two additional calculated parameters are also important to plant operators. The first parameter is Percent Recycle (also referred to as backset), which is the fractional percentage of recycled thin stillage (fermentation liquor output from a centrifuge that separates out cattle feed solids). Percent Recycle is managed manually to maintain both a rough thin stillage inventory and to operate within a range of fractional percent backset. It is important to manage the fractional percent backset, because the fermentation liquor contains both residual yeast nutrients along with yeast waste products from previous fermentation. Too little or too much backset can be a problem for fermentation productivity.

The second parameter is Fermentation Inventory, which is a totalized inventory across the filling, draining and fermenting fermentation vessels and key auxiliary equipment. If this total inventory level is held within an acceptably stable band, the front plant section, i.e., the milling/cooking, and fermentation processes, can be managed to match the back plant section, i.e., the distillation and stillage processes, across all batch sequentially operated fermentation vessels. If totalized batch volume is constant, then filling is balanced with draining across multiple parallel batch fermentation vessels.

A biofuel production plant may require numerous adjustments, e.g., on a minute-to-minute basis, in response to changes and shifting constraints if the plant process is to operate in an optimal manner. Due to this complexity, human operators are not capable of actively optimizing a biofuel production process. Consequently, operators generally operate a plant in a less efficient operating mode.

Thus, improved systems and methods for biofuel production are desired.

SUMMARY OF THE INVENTION

Embodiments of a system and method are presented for managing a fermentation feed in a biofuel production process. In one embodiment, the system may include a dynamic multivariate predictive model-based controller coupled to a dynamic multivariate predictive model of biomass concentration and water inventory for the fermentation feed of the biofuel production process.

The dynamic multivariate predictive model of biomass concentration and water inventory for the fermentation feed of the biofuel production process may be executable to:

receive water inventory and biomass information from the biofuel production process; receive a specified objective for the fermentation feed specifying a target biomass concentration for the fermentation feed; and generate model output comprising target values for a plurality of manipulated variables of the biofuel production process, including target flow rates of water and/or biomass contributing to the fermentation feed in accordance with the specified objective.

The dynamic multivariate predictive model-based controller may be operable to dynamically control the biofuel production process by adjusting the plurality of manipulated variables to their model determined target values to stabilize water/biomass balance in the fermentation feed in accordance with the specified objective, including the specified target biomass concentration.

In one embodiment, the method may include providing a dynamic multivariate predictive model of biomass concentration and water inventory for a fermentation feed of the biofuel production process; receiving a specified objective for the fermentation feed specifying a target biomass concentration for the fermentation feed; receiving water inventory information and biomass concentration information from the biofuel production process; executing the dynamic multivariate predictive model in accordance with the objective using the received water inventory and biomass concentration information as input, thereby generating model output including target values for a plurality of manipulated variables of the biofuel production process, including target water and/or biomass flow rates contributing to the fermentation feed in accordance with the objective; and controlling the biofuel production process, including water and/or biomass flow rates related to the fermentation feed of the biofuel production process, in accordance with the plurality of manipulated variables to stabilize water/biomass balance in the fermentation feed in accordance with the specified objective, including the specified target biomass concentration.

In some embodiments, the dynamic multivariate predictive model may include one or more of: a linear model; a nonlinear model; a fundamental model; an empirical model (comprising one or more of: a neural network; and/or a support vector machine); a statistical model; a rule-based model; and/or a fitted model.

In some embodiments, the method may further include: receiving constraint information specifying one or more constraints; and executing the dynamic multivariate predictive model in accordance with the objective using the received water inventory, the one or more constraints, and biomass concentration information as input, thereby generating model output in accordance with the objective and subject to the one or more constraints.

In some embodiments, controlling flow rates of water inventory and/or biomass concentration may include operating one or more flow controllers coupled to the dynamic multivariate model-based controller, where the one or more flow controllers control one or more of: mill speed, pump speeds for one or more biomass feeds, and/or pump speeds for one or more water feeds.

In some embodiments, water inventory information may include one or more of: fluid levels for one or more water tanks, capacity limits for each of the one or more water tanks, operational status for each of the one or more water tanks, and/or flow rates for one or more water flows. Water inventory information may also include inventory information for a plurality of water sources, including one or more of: one or more water sources and/or one or more recycled water sources, and target water flow rates may include target flow rates for one or more of: water and/or recycled water.

In some embodiments, biomass concentration information may include one or more of: feed rates for each mill, amp limits for each mill, water flow rates, stream density, temperature and/or biomass concentration limit.

In some embodiments, the dynamic multivariate predictive model may specify relationships between fermentation feed rates and equipment constraints of the biofuel production process, the dynamic multivariate predictive model may receive the one or more equipment constraints as input, and the target water and/or biomass flow rates may be computed to approach and maintain the target feed rate for the fermentation feed subject to the one or more equipment constraints.

In some embodiments, the objective for the fermentation feed may be specified by a human operator and/or a program.

In some embodiments, the dynamic multivariate predictive model may specify relationships between biomass fractional flow rates and enzyme flow rates and may receive enzyme flow rate information from the biofuel production process including one or more enzyme flow rates. The dynamic multivariate predictive model may output target enzyme flow rates to stabilize water/biomass and enzyme/biomass balance in the fermentation feed.

In some embodiments, the dynamic multivariate predictive model may include one or more temperature control constraints for the biofuel production process. The method may include: receiving one or more temperature targets, receiving temperature information from the biofuel production process, executing the dynamic multivariate predictive model using the temperature information as input subject to the one or more temperature control constraints to output target temperature values, and controlling temperatures related to the fermentation feed of the biofuel production process in accordance with the target temperature values to stabilize water/biomass and enzyme/biomass balance in the fermentation feed.

In some embodiments, the dynamic multivariate predictive model may include pH relationships in the biofuel production process. For example, the pH relations in the biofuel production process may include relations between pH and one or more of: mixing tank level of a pH control agent with slurry, ambient temperature, time of day, solids content of the fermentation feed, liquid temperature of the fermentation feed, and/or slurry flow rate of the fermentation feed, among others. The method may include receiving pH information from the biofuel production process, executing the dynamic multivariate predictive model using the pH information as input to output a target pH for the fermentation feed and a pH control agent target, and controlling pH related to the fermentation feed of the biofuel production process in accordance with the target pH and pH control agent target. In various embodiments, the pH information may include one or more of: the mixing tank level of the pH control agent with slurry, the ambient temperature, the time of day, the solids content of the fermentation feed, the liquid temperature of the fermentation feed, and/or the slurry flow rate of the fermentation feed, among others.

BRIEF DESCRIPTION OF THE DRAWINGS

A better understanding of the present invention can be obtained when the following detailed description of the preferred embodiment is considered in conjunction with the following drawings, in which:

FIG. 7 is a high-level block diagram of a system for managing a fermentation feed from a milling/cooking sub-process of a biofuel production process utilizing model predictive control, according to one embodiment.

Figure 1:
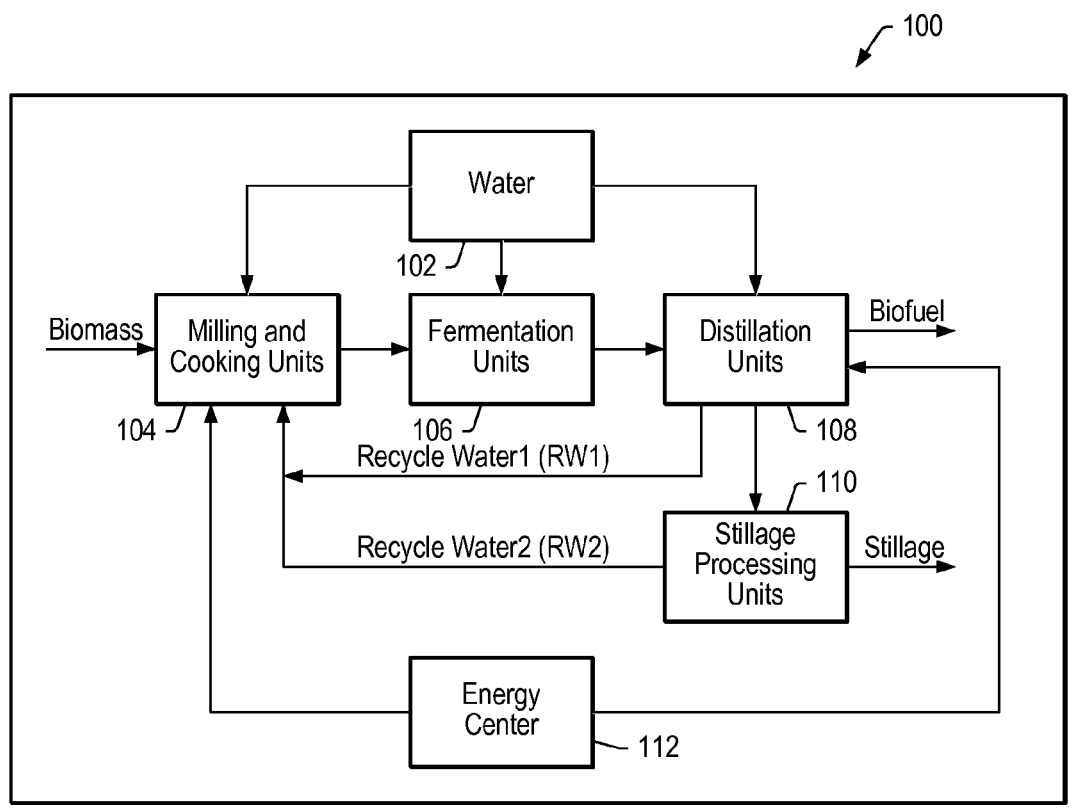
FIG. 1 illustrates one example of a biofuel processing plant, according to the prior art.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF THE INVENTION

Definitions—Biofuel Production Processes

Biofuel—any fuel (or fuels) derived from biomass, i.e., from recently living organisms or their bi-products.

Biofuel production process—a fermentation process surrounded by auxiliary processing units to produce biofuel, other fermentable alcohols for fuel, and high-capacity food grade or chemical grade alcohols.

Biofuel production—a measure of biofuel production within or at the end of a production process. May include measurements such as concentration (e.g., wt. %, volume % or wt./vol. %), volume (e.g., current gallons biofuel within a fermenter) or mass (e.g., current kg biofuel within a fermenter).

Batch processing—a staged discontinuous processing step that includes a start and an end, in contrast to continuous processing that continues without stop, e.g., during a normal operating day or week. Continuous processing is generally represented by fairly steady targets or operations, where at least some parameters change throughout batch processing. For example, biofuel production, e.g., fermentation, starts at low levels at the start of a batch and increases throughout the batch with or without a drop at the end representing degradation rates being higher than production rates. Similarly, yeast cellular concentrations, start at fairly low levels, and generally grow throughout a batch, although they generally have a lag (relatively constant concentrations), exponential growth, stable growth, and degradation phase within a batch.

Slurry—a fermentation feed mash comprising a two-phase (liquid and solid) slurry that will be fermented.

Solids or % solids—fraction or percent of solids in the fermentation feed.

Milling and Cooking Process—continuous processing for pre-fermentation of the fermentation feed, which generally includes grain or cane milling, cooking, mixing with water and processing chemicals, cooking for sterilization and increasing water concentration within solids, and other pre-fermentation processing.

Biomass concentration—content attribute of the fermentation feed specified by one or more of: slurry solids, liquefaction solids, slurry density, liquefaction density, slurry % or fraction carbohydrates, and slurry % or fraction fermentable sugar.

Water inventory information—includes water flows, recycle liquid flows, evaporator condensate recycle flow, thin stillage or centrifuge liquor recycle flows, water addition flows, processed water addition flows, slurry flows, mash flows, and various levels or weights for various tanks used to hold inventories of these flows or for intermediate receptacles (e.g. methanator feed tank, slurry feed tank, liquefaction tank, distillate tank, grain silo inventories or other biomass inventories, etc.).

Liquefaction—for grains with high starch content, the starch is liquefied to reduce its carbohydrate chain length and viscosity by adding enzymes or other biologic agents.

Thermal Oxidizer/Heat Recovery Steam Generator (HRSG)—process equipment that is used to destroy volatile organic compounds (VOCs), to reduce air and remove stenches from stillage dryer or evaporation systems. The heat recovery steam generator is used to recover the heat required to destroy the VOCs, and is typically the energy center of the biofuels production process.

Dried Distillers Grains (DDG)—post fermentation solid residue that includes undigested grain residue, other solid residues (enzymes, salts), and yeasts (or other cellular residue) that may be dried and released as a production by-product (generally as animal feed). DDG may also be used herein to include WDG (wet distillers grains), which are only partially dried for local consumption (e.g. without long-term biological stability) and DDGS/WDGS (dried distillers grains with solubles and wet distillers grains with solubles). Solubles includes residue solids that are soluble in water and therefore present in stillage concentrate. Solubles may be partially concentrated (generally with evaporation), and added to DDG or WDG to increase yields and manage by-product inventories.

Enzyme—highly selective biological-based catalyst added to manage specific reactions within a fermentation process. The most common enzymes used today include alpha amylase to rapidly break starches into dextrins, gluco-amylase to break dextrins into glucose, and proteases to break grain proteins into digestible proteins to support cell growth. In the same way as described below, modeling and controlling starch-based fermentations, enzymes specific for cellulosic conversion into biofuels or other enzymes affecting yeast (see below), growth or nutrient availability may be managed.

Yeast—a biofuel producing organism. Yeasts are currently the most commonly used organism in ethanol production although other biofuel producing organisms including genetically engineered *E. coli* can be substituted throughout as the technology described may not be specific to yeast, and may apply to many organisms used in fermentation processes to produce biofuel.

Stillage/Whole Stillage—non-fermentable solids and water liquid removed from the bottom of the primary distillation units.

Thin Stillage—the separated liquid from the stillage non-fermentable solids.

Syrup—concentrated thin-stillage with a large portion of the moisture removed. The % solids in syrup are usually in the range of 20-45% solids, but percentages outside this range may occur.

Azeotrope—a special mixture of two compounds, that when in equilibrium, the vapor phase and liquid phase have exactly the same compositions. This makes it difficult to separate the two components to achieve a better purity. Special separation processes are required to break the azeotrop. They comprise azeotropic distillation (add a $3^{rd}$ compound to break the azeotrop), extractive distillation (use a solvent to separate the 2 compounds), or molecular sieve technology (preferentially trap molecules of one component in a molecular sieve bed as the other component passes over the molecular sieve bed).

Volatile Organic Compounds (VOCS)—Organic compounds that tend to vaporize when subject to atmospheric pressure and ambient temperature ranges.

Capacity—capacity is the established maximum production rate of the process, sub-process, or unit under best operating conditions (no abnormal constraints). Capacity is generally a constant within the present capital investment. For new units it is the vendor's specified capacity. For established units, capacity is established by demonstrated historical production rates.

Model—an input/output representation, which represents the relationships between changes in various model inputs and how the model inputs affect each of the model outputs.

Dynamic Predictive Model—an input/output representation of a system or process that not only reflects how much an output changes when an input is changed, but with what velocity and over what time-dependent curve an output will change based on one or more input variable changes. A dynamic multivariate predictive model is a dynamic predictive model that represents or encodes relationships among multiple parameters, and is operable to receive multiple inputs, and generate multiple outputs.

Model Predictive Control (or MPC)—use of multivariate dynamic process models to relate controller objectives (targeted controller outputs and constraints) with regulatory controllers (existing single-input/single-output controllers such as ratio flow, temperature, level, speed, or pressure controllers) over a predicted time interval (e.g., 1 minute, 30 minutes, 2 hours, 100 hours, etc.).

Objective Function—encodes an objective that sets the goal or goals for the overall operation of the process, sub-process, or unit. The objective function provides one or more consistent numerical metric(s) to which the process, sub-process, or unit strives to achieve and over which the performance of the process, sub-process, or unit may be measured, e.g., from a business.

Control Variables—(also called controlled variables) those variables that the controller/optimizer tries to bring to a specified value, e.g., to a target value, maximum, etc.

Integrated Variables—integrated control variables are variables that are not stable, but integrate generally with a stable first derivative as a function of time. The most common integrated variable is a tank level where as long as inputs and outputs are imbalanced the level will increase or decrease. Thus, when balanced a change in an input or output flow will cause a tank to either overfill or drain as integrated over time. A controller must use these integration calculations to determine when and how rapidly input or output flows must be adjusted.

Manipulated Variables—those variables over which the management of the process or unit has authority and control, e.g., via regulation of the process with online controllers, and which are changed or manipulated by the controller/optimizer to achieve the targets or goals of the control variables. These variables are the actual control variables whose values are limited by the constraints. This is in distinction from controllable constraints in the sense that manipulated variables may operate within some range of controllable or fixed constraints. Manage is an alternate term for process control.

Disturbance Variable—a variable representing an external influence on a process that, in addition to objective variables and regulatory controllers, is outside the controller scope, and so it acts on the objective variables, but independently of the described controller. Disturbance variables are used in feed-forward disturbance rejection. Disturbance variables are also measured or unmeasured variables over which the management of the process or unit does not have direct authority or control. For example, temperature, humidity, upstream flow, or quality, may all be referred to as measured disturbance variables.

Set Point (targets)—also "setpoint"; the target signal or value for a manipulated variable or targeted controlled variable.

Constraints—Constraints represent limitations on particular operating variables or conditions that affect the achievable production rate of a production unit. Constraints are of two types: controllable and external, defined below. Constraints may include, but are not limited to: safety constraints, equipment constraints, equipment availability constraints, personnel constraints, business execution constraints, control constraints, supply chain constraints, environmental permit and legal constraints. Safety constraints ensure the safety of equipment and personnel. Equipment constraints, such as the maximum open position of a control valve, maximum tank capacity, etc., may limit the physical throughput of the unit. Equipment availability constraints may include, but are not limited to: readiness due to maintenance planning and scheduling, or due to unexpected equipment outages, authorized production level set by the supply chain and production scheduling systems. Personnel constraints refer to limitations on the availability of staffing and support functions, business rules and constraints imposed by contract and policy. Business execution constraints are limits imposed by the time required to execute associated business and contractual tasks and obligations. Control constraints are limits on the maximal position and rate of change of manipulated variables. Supply chain constraints are limits on the availability of raw materials, energy, and production supplies. Environmental permit and legal constraints are limits on air emissions, wastewater, waste disposal systems, and/or environmental constraints imposed upon the performance of the unit, such as river levels and current weather imposed limitations.

Controllable Constraints—constraints imposed on the performance of a process or unit over which the management of the process or unit does have authority and discretionary control. For example, the separation in a distillation tower may be affected by distillation tray fouling. The tray fouling is a function of how the feedstock is processed, and how often the unit is taken offline for cleanup. It is management's discretion as to when the unit is serviced. Controllable constraints change a unit's throughput capacity.

External Constraints—limitations imposed on the performance of the process, sub-process, or unit over which the management of the process, sub-process, or unit does not have authority or discretionary control. These external constraints come in two types: external constraints that are controllable by other entities or processes in the plant or in the supply chain, and those constraints that are imposed by physical, safety, environmental, or legal constraints and are not controllable by anyone in the plant or supply chain.

System—a system may be defined by the inputs and the characteristics of the system or process. In the biofuel production process, the system may be defined for: the entire biofuel production process, a sub-process of the biofuel production process such as the milling and cooking process, or control of a variable in a sub-process such as the cooking temperature.

Figure 2:
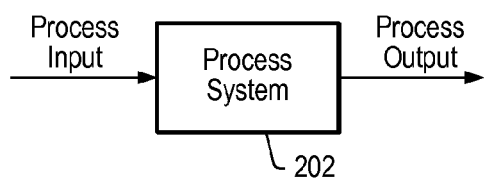
FIG. 2 illustrates an open loop process system, according to the prior art.
Figure 3:
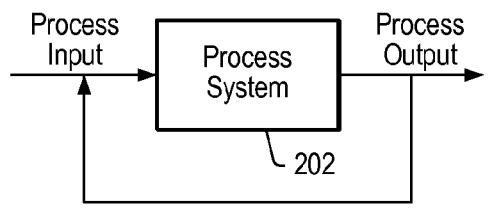
FIG. 3 illustrates a closed loop process system, according to the prior art.

Open Loop Systems—are systems that respond to an input, but the system is not modified because of the behavior of the output (see FIG. 2). For example, in a biofuel system, a reciprocating pump will operate and move at a fixed volume of syrup independent of the upstream and downstream pressure if the reciprocating pump does not have a pressure control system.

Closed Loop Systems—system inputs may be adjusted to compensate for changes in the output. These changes may be a deviation from an objective for the system, impacts of constraints on the system or system variables, or measurements of output variables. The closed loop system may be used to sense the change and feedback the signal to the process input. In biofuel systems, closed loop systems may predominate, since these systems may be regulated subject to constraints such as production (product) quality, energy costs, process unit capacity, etc.

Control Variables—Control variables (also called controlled variables) are those variables that the controller/optimizer tries to bring to some objective, e.g., to a target value, maximum, etc.

Manipulated Variables—Manipulated variables are those variables over which the management of the process or unit has authority and control, and which are moved or manipulated by the controller/optimizer to achieve the targets or goals of the control variables. These variables are the actual control variables whose settings are limited by the constraints. This is in distinction from controllable constraints in the sense that manipulated variables may operate within some range of controllable or fixed constraints.

Control System—the regulatory level mechanism by which the manipulated variables are driven to the set points.

Response—the measurement of the current position of the manipulated variable. The response is the feedback of the movement of the manipulated variable to the set point in response to the actions of the control system in its effort to achieve the set point.

Target Profile—a desired profile or trajectory of variable values, i.e., a desired behavior of a control variable or a manipulated variable.

Control Horizon—the period of the time extending from the present into the future during which one plans to move or change manipulated variables. Beyond this horizon the MV is assumed to stay constant at its last or most recent value in the control horizon.

Prediction Horizon—the period of time extending from the present into the future during which the process or system response is monitored and compared to a desired behavior.

Biofuel Production Process

Figure 4:
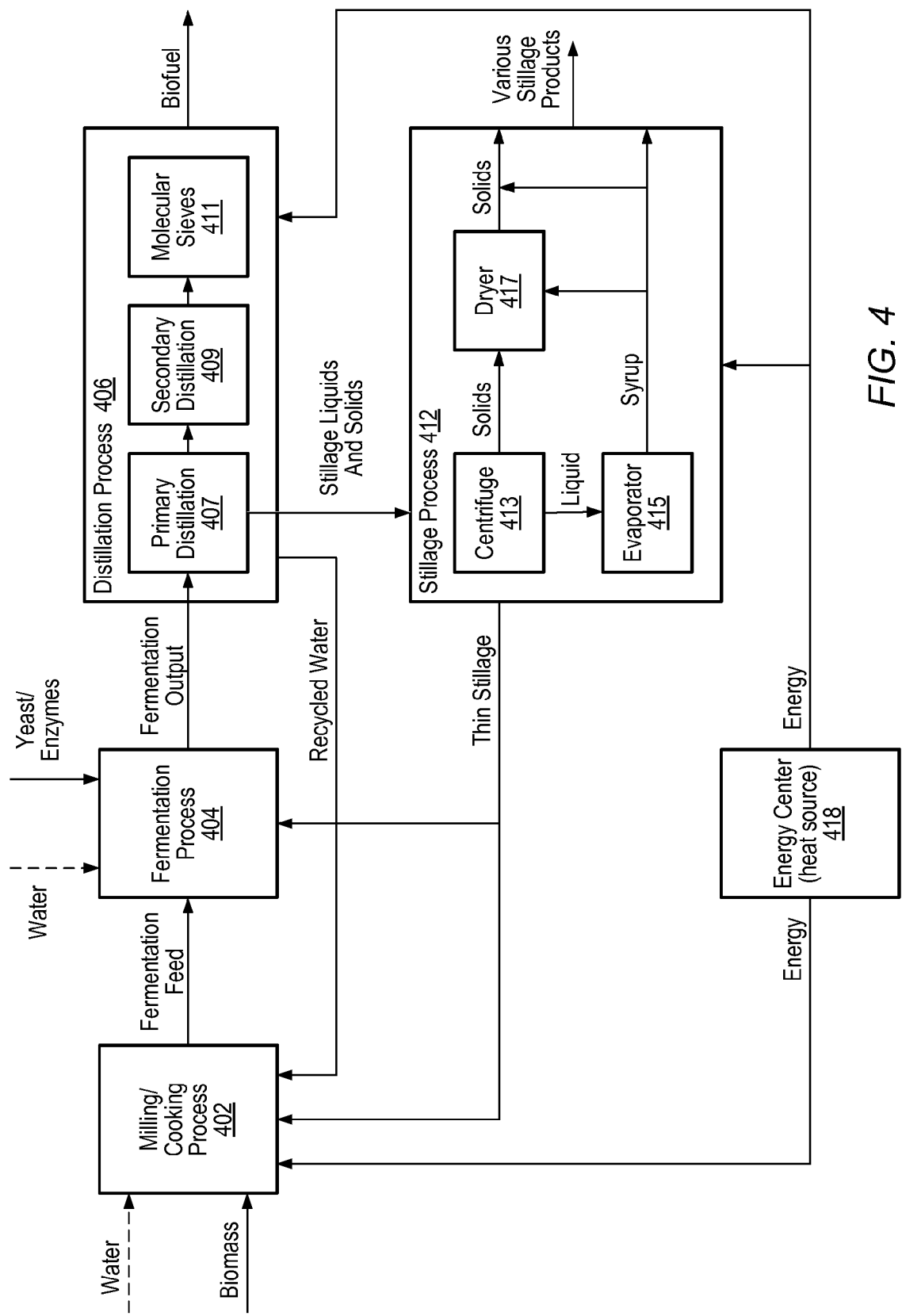
FIG. 4 illustrates an exemplary high-level processing flow schematic of plant sections of a biofuel processing plant, according to one embodiment.

FIG. 4 illustrates an exemplary high-level processing flow schematic of sub-processes of a biofuel production process, according to one embodiment. It should be noted that the particular components and processes shown are meant to be exemplary only, and are not intended to limit embodiments of the invention to any particular set of components or processes.

As FIG. 4 indicates, a milling/cooking process 402 may: receive water, biomass, energy (electrical and/or thermal), recycled water, and/or recycled thin stillage; mill the biomass; cook the mixture; and output a biomass slurry (referred to as a fermentation feed) to a fermentation process 404. The fermentation process 404 may: receive the biomass slurry, water, yeast, enzymes, and recycled thin stillage; ferment the mixture; and output fermentation products to a distillation process 406. The distillation process 406 may: receive the fermentation products, remove water and stillage (liquid and solid stillage) from the fermentation products in a one to three step process (e.g., primary distillation 407, secondary distillation 409, and/or molecular sieves (dryers) 411), recycle water removed from the fermentation products to the milling/cooking process 402, output the liquid and solid stillage to a stillage process 412, and output biofuel products. The stillage process 412 may: receive the liquid and solid stillage, process the liquid and solid stillage (utilizing one or more of centrifuge dryers 413, other dryers 417, and/or evaporators 415) to produce and output various stillage products, and recycle thin stillage liquid to the fermentation process 404 and the milling/cooking process 402. An energy center 418 may provide electric power and heat (steam) to the various sub-processes as shown in FIG. 4.

One or more of the processes described above may be managed and controlled via model predictive control (MPC) utilizing a dynamic multivariate predictive model that may be incorporated as a process model in a dynamic predictive model-based controller. Model predictive control of a sub-process of a biofuel production process is described below, first for a generic sub-process and then in more detail for the milling/cooking process 402, specifically directed to managing the fermentation feed provided by the milling/cooking process 402 to the fermentation process 404.

MPC Applied to a Sub-Process of a Biofuel Production Process

Various embodiments of systems and methods for applying model predictive control (MPC) to a biofuel production process are described below. In this approach to biofuel production, a dynamic multivariate predictive model may be incorporated as a process model in a dynamic predictive model-based controller. This MPC system may project or predict what will happen in the production process (e.g., in the near future) based on the dynamic prediction model and recent process history, including, for example, recent operating conditions or state values. This projection or prediction may be updated or biased based on received current process information, specified objectives, and/or system or method constraints. Control algorithms may be used to recursively or iteratively estimate the best current and future control adjustments on the model inputs to achieve a desired output path. Targets set on the dynamic model outputs may be compared to how that output may behave over a predictive future horizon and the best available controllable model input adjustments may be estimated to best achieve the controller targets.

It should be noted that the biofuel or biofuels produced by embodiments of the methods described herein may be any biofuel generated from biomass, and that the types of biomass contemplated may be of any type desired, including, but not limited to, grains (e.g., corn, wheat, rye, rice, etc.), vegetables (e.g., potatoes, beats, etc.), canes (e.g., sugarcane, sorghum, etc.), and other recently living organisms and/or their bi-products.

Figure 5:
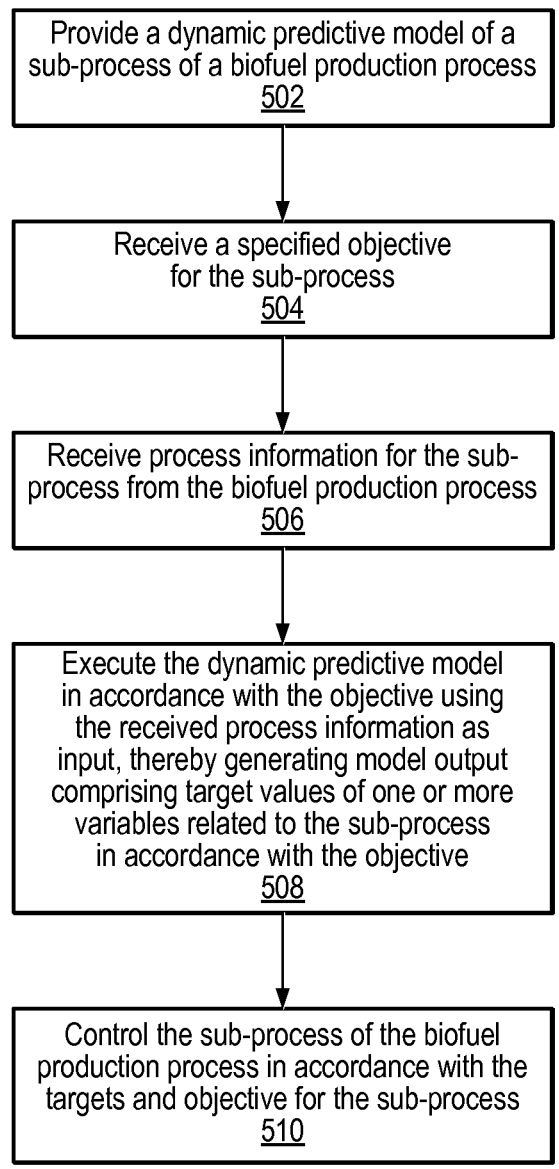
FIG. 5 is a high-level flowchart of a method for managing a sub-process of a biofuel production process utilizing model predictive control, according to one embodiment.

FIG. 5 is a high-level flowchart of a computer-implemented method for managing a sub-process of a biofuel production process utilizing model predictive control (MPC), according to one embodiment. As used herein, the term biofuel refers to one or more biofuel products output from a biofuel production process. It should be noted that embodiments of the method of FIG. 5 may be used with respect to any sub-process of a biofuel production process desired (e.g., milling/cooking, fermentation, distillation, and/or stillage processing), as well as combinations of such sub-processes. In various embodiments, some of the method elements shown may be performed concurrently, in a different order than shown, or may be omitted. Additional method elements may also be performed as desired. As shown, this method may operate as follows.

In 502, a dynamic multivariate predictive model (also referred to as a dynamic predictive model) of a sub-process of a biofuel production process may be provided. In other words, a model may be provided that specifies or represents relationships between attributes or variables related to the sub-process, including relationships between inputs to the sub-process and resulting outputs of the sub-process. Note that the model variables may also include aspects or attributes of other sub-processes that have bearing on or that influence operations of the sub-process.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard MPC models (i.e., fitted models generated by functional fit of data), and/or hybrid models using any combination of the above models.

In 504, an objective for the sub-process may be received. The objective may specify a desired outcome, result, behavior, or state, of the sub-process, such as, for example, a desired throughput, quality, efficiency, product profile, behavior, or cost, among others. In preferred embodiments, the objective may specify at least one targeted measurable attribute defining product quality for the sub-process (or the overall production process). Note that an objective may be a specific value, such as a specified percent solids for a fermentation feed, a specified temperature of a fermentation vat, etc., or may be a specified extremum, i.e., a maximum or minimum of an attribute, such as, for example, minimizing cost, maximizing production, etc. Moreover, in some embodiments, an objective may include multiple components, i.e., may actually comprise a plurality of objectives and/or sub-objectives. In some embodiments, the objective may involve multiple variables, e.g., a ratio of variables. Moreover, in some embodiments, there may be a global objective, e.g., maximize production or profit, and multiple sub-objectives that may in some cases be at odds with the global objective and/or one another.

In 506, process information for the sub-process of the biofuel production process may be received. In other words, information related to the sub-process may be received, e.g., from the sub-process (or from other portions of the biofuel production process that influence the sub-process), and/or from other sources, e.g., a laboratory, inferred property models (that model variables that are not readily measurable), external systems, or any other source as desired. This information generally includes data from one or more sensors monitoring conditions of and in the sub-process (e.g., temperatures, pressures, flow rates, equipment settings, and so forth), although any other information germane to the sub-process may be included as desired (e.g., constraints to which the sub-process may be subject, ambient conditions of the biofuel process, economic or market data, and so forth).

In 508, the model may be executed in accordance with the objective for the sub-process using the received process information as input, thereby generating model output comprising target values for one or more manipulated variables related to the sub-process in accordance with the objective for the sub-process. In other words, the model may be executed with the received processing information as input, and may determine target values of one or more controllable attributes of the sub-process in an attempt to meet the specified objective for the sub-process (which could be a global objective for the entire biofuel production process). For example, in an embodiment where the objective is to maximize output for the sub-process, the model may determine various target values (e.g., sub-process material input flows, temperatures, pressures, and so forth) that may operate to maximize the output. As another example, in an embodiment where the objective is to minimize waste for the sub-process, the model may determine target values that may operate to minimize waste for the sub-process, possibly at the expense of total output. In a further example, the objective may be to maximize profit for the entire production process, where maximizing output and minimizing waste may be two, possibly competing, sub-objectives, e.g., included in the objective.

As is well-known in the art of model predictive control, in some embodiments, the execution of the model in 508 may include executing the model in an iterative manner, e.g., via an optimizer, e.g., a nonlinear optimizer, varying manipulated variable values (which are a subset of the model inputs) and assessing the resulting model outputs and objective function, to determine values of the manipulated variables that satisfy the objective subject to one or more constraints, e.g., that optimize the sub-process subject to the constraints, thereby determining the target values for the manipulated variables.

In 510, the sub-process of the biofuel production process may be controlled in accordance with the corresponding targets and objective for the sub-process. Said another way, a controller coupled to the dynamic multivariate predictive model may automatically control various (controllable) aspects or variables of the sub-process according to the target values output by the predictive model to attempt to achieve the specified objective.

The method of FIG. 5 may be repeated, e.g., at a specified frequency, or in response to specified events, so that the process may be monitored and controlled throughout a production process, or throughout a series of production processes. In some embodiments, the period or frequency may be programmed or varied during the production process (e.g., an initial portion of a production process may have longer repetition periods (lower frequency), and a critical portion of a production process may have shorter repetition periods (higher frequency)).

Figure 6:
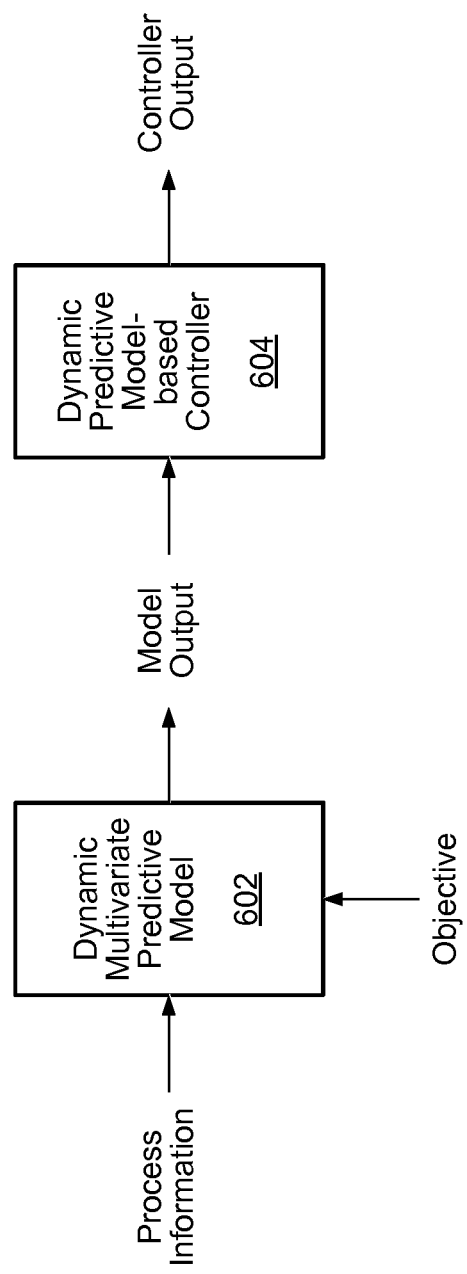
FIG. 6 is a high-level block diagram of a system for managing a sub-process of a biofuel production process utilizing model predictive control, according to one embodiment.

FIG. 6 illustrates an exemplary system for managing a sub-process of a biofuel production process, which may implement embodiments of the method of FIG. 5. The system may comprise: 1) a dynamic multivariate predictive model 602 (e.g., a predictive control model) of a sub-process in the biofuel production process; and 2) a dynamic predictive model-based controller 604 coupled to the dynamic multivariate predictive model 602. As described above with respect to FIG. 5 in more detail, the dynamic multivariate predictive model 602 may be executable to: receive an objective for a sub-process, receive processing information for the sub-process of the biofuel production process, execute the model in accordance with the objective for the sub-process using the received corresponding processing information as input, thereby generating model output comprising targets for one or more variables related to the sub-process in accordance with the objective for the sub-process. In addition, as described above with respect to FIG. 5 in more detail, the dynamic predictive model-based controller 604 may control the sub-process of the biofuel production process in accordance with the corresponding targets and objective for the sub-process. Process information may include measurements of a plurality of process variables, information on one or more constraints, and/or information about one or more disturbance variables related to the sub-process.

The following describes more specific embodiments of model predictive control of a sub-process of a biofuel production process according to the method of FIG. 5. Note, however, that the embodiments of the particular sub-process described are meant to be exemplary, and that such model predictive control may be applied to other embodiments of the described sub-process of the biofuel production process as desired.

Figure 8:
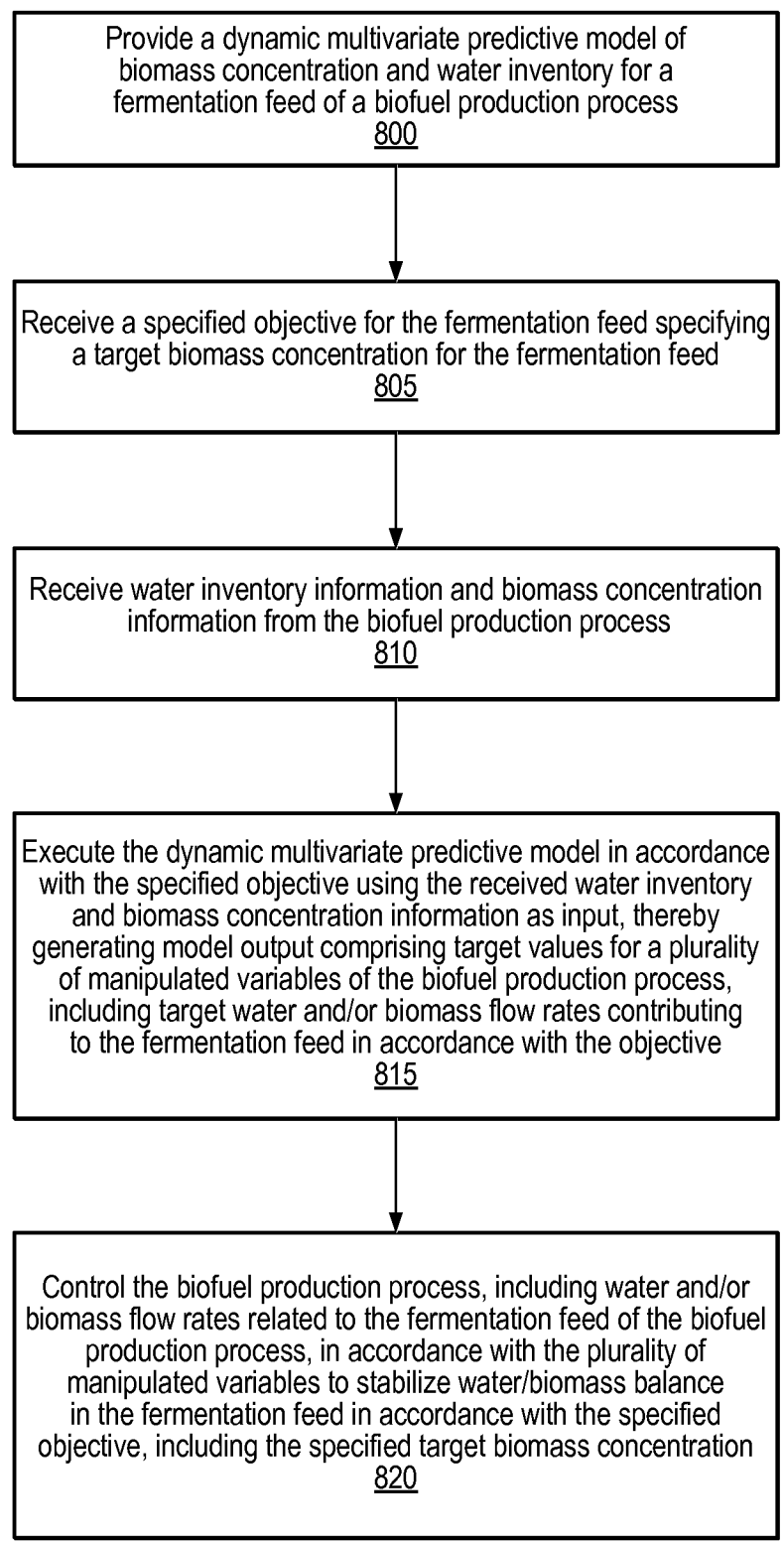
FIG. 8 is a high-level flowchart of a method for managing a fermentation feed from a milling/cooking sub-process of a biofuel production process utilizing model predictive control, according to one embodiment.

MPC Control of a Fermentation Feed of a Milling/Cooking Sub-Process in Biofuel Production FIGS. 7 and 8 are directed to model predictive control of a fermentation feed from a milling/cooking sub-process in a biofuel production process (e.g., the milling/cooking process 402 in FIG. 4). More specifically, FIG. 7 is a high-level block diagram of one embodiment of a system for managing the fermentation feed from a milling/cooking sub-process utilizing model predictive control to manage water inventory and biomass concentration for the fermentation feed in a biofuel production process. FIG. 8 is a high-level flowchart of one embodiment of a method for managing the fermentation feed from the milling/cooking sub-process utilizing model predictive control, where the milling/cooking sub-process provides a water/biomass slurry (the fermentation feed) to a fermentation process.

FIG. 7—System for MPC Control of a Milling/Cooking Sub-Process

As shown in FIG. 7, in one embodiment, a system for managing a fermentation feed in a biofuel production process may include: a dynamic multivariate predictive model 702 of biomass concentration and water inventory for a fermentation feed of the biofuel production process, and a dynamic predictive model-based controller 704 (also referred to as a dynamic multivariate predictive model-based controller) coupled to the dynamic multivariate predictive model 702.

The dynamic multivariate predictive model 702 may be executable to: receive process information (e.g., water inventory and biomass information) from the biofuel production process, receive a specified objective for the fermentation feed specifying a target biomass concentration for the fermentation feed, and generate model output including target values for a plurality of manipulated variables of the biofuel production process, including target flow rates of water and/or biomass contributing to the fermentation feed in accordance with the specified objective. The controller 704 may be operable to control the biofuel production process, including water and/or biomass flow rates related to the fermentation feed of the biofuel production process, in accordance with the plurality of manipulated variables to stabilize water/biomass balance in the fermentation feed in accordance with the specified objective, including the specified target biomass concentration. In some embodiments, the dynamic multivariate predictive model 702 may include a plurality of sub-models.

As noted above, the dynamic multivariate predictive model 702 may be incorporated as a process model in the dynamic predictive model-based controller 704, and may be executed to provide target values for manipulated variables. In this particular case, targets on biomass concentration and water inventories may be calculated by estimating the best, i.e., optimal or near optimal, current and future adjustments to water and biomass flow rates.

Model Predictive Control (MPC) may facilitate this best-case (i.e., optimal or near-optimal) achievement of projected future events, and may also enable multivariate balancing, so that, for example, levels across a series of tanks (included in the water inventory) may be controlled to achieve optimal or near optimal results within process constraints even with a transient imbalance due to coordination of batch and continuous operations. An MPC solution may have relative weighting factors to balance trade offs between competing objectives. For example, a tank level may be allowed to swing relatively freely within comfortable operating regions, but when the level forecast estimates that it may be nearly empty or near to over-filling, different limit weighting may be used to shift the control focus gradually from fractional water components in the fermentation feed to minimal corrections over a long dynamic horizon (e.g., 10 hours, 100 hours, etc.) that may avoid exceeding safe or comfortable operating states.

FIG. 8—Method for MPC Control of a Milling/Cooking Sub-Process

Embodiments of a method for managing fermentation feed in a biofuel production process are presented below. In one embodiment, as illustrated in FIG. 8, the method may include providing a dynamic multivariate predictive model of water inventory and biomass concentration for a fermentation feed of the biofuel production process 800; receiving a specified objective for the fermentation feed specifying a target biomass concentration for the fermentation feed 805; receiving water inventory information and biomass concentration information from the biofuel production process 810; executing the dynamic multivariate predictive model in accordance with the objective using the received water inventory and biomass concentration information as input, thereby generating model output comprising target values for a plurality of manipulated variables of the biofuel production process, including target water and/or biomass flow rates contributing to the fermentation feed in accordance with the objective 815; and controlling the biofuel production process, including water and/or biomass flow rates related to the fermentation feed of the biofuel production process, in accordance with the plurality of manipulated variables to stabilize water/biomass balance in the fermentation feed in accordance with the specified objective, including the specified target biomass concentration 820.

Various embodiments of the method stated above and illustrated in FIG. 8 are discussed below in more detail. FIG. 8 is a high-level flowchart of a computer-implemented method for managing a sub-process of a biofuel production process utilizing model predictive control (MPC), according to one embodiment. In various embodiments, some of the method elements shown may be performed concurrently, in a different order than shown, or may be omitted. Additional method elements may also be performed as desired. As shown, this method may operate as follows.

Provide a Model

In 800 of FIG. 8, a dynamic multivariate predictive model of the milling/cooking sub-process of a biofuel production process may be provided. In other words, a model may be provided that specifies or represents relationships between attributes, inputs, and/or other variables of the milling/cooking sub-process as related to water inventory and a biomass concentration of a fermentation feed (the output of the milling/cooking sub-process). Note that the model variables may also include aspects or attributes of other sub-processes that have bearing on or that influence operations of the sub-process.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard MPC models (i.e., fitted models generated by functional fit of data), and/or hybrid models using any combination of the above models.

As is well known to those of skill in the art of model predictive control, a dynamic multivariate predictive model is a set of process mathematical relationships that includes steady state relationships (e.g., mill flow 1+mill flow 2+recycle water=total slurry flow), and also includes the time lag relationship for each parameter change to be realized in the output (e.g., a change in mill flow 1 may have a time lag of two minutes, after which it may respond using first order dynamic models with a time constant of six minutes as it affects the measured slurry flow). A large variety of dynamic relationships may be possible, and each relationship between variables may be characterized by how much one variable affects another, and also by how fast the affects occur.

The model may be created from a combination of relationships based on available data such as: vessel volumes and fundamental dynamic and gain relationships, sufficiently available and moving plant historic process data, and supplementary plant testing on variables that cannot be identified from the two previous steps. Models may be customized to the plant layout and design, critical water inventories, plant constraints and measurements, and controllers available to manage biomass concentrations. In preferred embodiments, the dynamic multivariate predictive model may be a multivariable predictive control model.

An important characteristic of a dynamic model may be to identify when conditions of the fermentation feed will change at a particular point of measurement. In other words, the model may identify the time-response (e.g., time lag) of one or more attributes of the fermentation feed with respect to changes in control variables. For example, once a controller adjusts water rates there may be a certain time-dependent response before observing an affect at the mixing location and even later in the fermentation feed. This time-dependent response may be unique for each independent controller (i.e., water may take longer to mix with the slurry than recycled fermentation liquids because of differences in system variables (e.g., piping lengths, tank volumes, etc.) between the control actuator and flow sensor and the mixing point).

Water inventory levels and individual water sources fractions may be managed through calculations of the dynamic model, but there may be other process disturbances that may be unmeasured. For example, consider a situation where a level starts to rise out of balance with filling demand, e.g., because of manual plant changes (e.g., scheduled equipment cleaning that involves draining and/or filling specific tankage)—the dynamic model may be made aware of an imbalance so that corrective actions may be made gradually to avoid dramatic or fermentation-critical actions being made. This may be an issue for many of the tanks that have both batch and continuous plant operations in sequence. Specific tankage may be used to provide storage capacity to facilitate balancing and avoid continuous out-of-control operations after every batch action. Because batch vessels drain rapidly, specific tank volumes may be difficult to run in automatic level control. This described real-time receipt of current vessel and material balance information (flows and levels) may provide an update on current equipment status and the execution of the dynamic model may enable projections to be made to avoid both emptying/over-filling vessels and emergency large flow moves to correct imbalances.

Receive a Specified Objective

In 805 of FIG. 8, a specified objective for the fermentation feed specifying a target biomass concentration for the fermentation feed may be received.

A specified objective for the fermentation feed may include a desired behavior, attribute, or result of the fermentation feed (e.g., at least one targeted measurable attribute defining product quality for the fermentation feed). In one embodiment, the specified objective may include one or more of: one or more-operator specified objectives; one or more predictive model specified objectives; one or more programmable objectives; a target feed rate for the fermentation feed; one or more cost objectives; one or more quality objectives; one or more equipment maintenance objectives; one or more equipment repair objectives; one or more equipment replacement objectives; one or more economic objectives; a target throughput for the biofuel production process; one or more objectives in response to emergency occurrences; one or more dynamic changes in water inventory information; one or more dynamic changes in biomass concentration information; and/or one or more dynamic changes in one or more constraints on the biofuel production process.

In some embodiments, the objective for the fermentation feed may be specified by a human operator and/or a program.

In some embodiments, the objective may include one or more sub-objectives. The sub-objectives may include one or more of: a target fermentation feed rate, a consistent fermentation residual broth fraction of the fermentation feed, and/or a consistent water fraction of the fermentation feed.

In one embodiment, the objective may include constraint information specifying one or more constraints, i.e., limitations on various aspects, variables, or conditions, related to the fermentation feed. In one embodiment, the constraint information may include dynamic constraint information. In one embodiment, the one or more constraints may include one or more of: water constraints, biomass constraints, feed constraints, equipment constraints, capacity constraints, temperature constraints, pressure constraints, energy constraints, market constraints, economic constraints, and/or operator imposed constraints, among others. In one embodiment, the one or more constraints may include one or more of: mill amperage limit that limits fermentation feed rate and/or cook flow rate, thin stillage tank level limits that limit fermentation residual broth recycle rate, slurry water tank level limits that limit water addition rates, back-end processing rate limits that limit fermentation fill rate, and/or cook temperature limits that limit fermentation fill rate.

In one embodiment, the one or more constraints may also include equipment constraints comprising one or more of: operating limits for pumps, operational status of pumps, tank capacities, operating limits for tank pressures, operational status of tanks, operating limits for valve pressures, operating limits for valve temperatures, equipment amp limits, and/or operating limits for pipe pressures, among others. Thus, in some embodiments of the invention, the dynamic multivariate predictive model may specify relationships between fermentation feed rates and equipment constraints, where the constraint information may include one or more equipment constraints of the biofuel production process.

In one embodiment, the dynamic multivariate predictive model may comprise a multivariate predictive model that represents relationships between the one or more constraints, the objective, including any sub-objectives, and the plurality of manipulated variables.

Receive Process Information

In 810 of FIG. 8, process information may be received. In one embodiment, the process information may include receiving water inventory information and biomass concentration information from the biofuel production process.

In some embodiments, water inventory information may include one or more of: fluid levels for one or more water tanks, capacity limits for each of the one or more water tanks, operational status for each of the one or more water tanks, and/or flow rates for one or more water flows. The one or more water flows may include one or more of: water flow rates to each of one or more processing units, recycled water flow rates from one or more distillation units, and/or recycled water flow rates from one or more stillage processing units.

Water inventory information may also include inventory information for a plurality of water sources, comprising one or more of: one or more water sources and/or one or more recycled water sources, and target water flow rates may include target flow rates for one or more of: water and/or recycled water. Recycled water may include one or more of: fermentation broth recycle water, evaporator condensate recycle water, distillation bottoms recycle water, and/or treated water from an anaerobic digester.

Water inventory information may include any vessel, tank or plant capacitance (possibly including transport mechanisms such as water pipes) reflected in control system calculations or measurements (e.g., tank level %, level ft, level kg, volume, etc.) that may be a holding volume for a fermentation water content component. Examples include: thin stillage tanks (to store fermentation residue liquor from a centrifuge after it has extracted the majority of suspended residual solids), evaporator condensate tanks (to store condensed water evaporated off concentrated thin stillage to pre-concentrate the fermentation residue liquor for sale or for adding to distillers grain), distillation column bottoms water inventory that may be recycled to the milling/cooking sub-process, methanator feed tank or other holding tank that contains water that may be fed to a water treatment plant prior to adding back to the fermentation feed (e.g., anaerobic or aerobic digester), cooking feed tank, and/or overall holding tank for multiple recycled and other water streams, among others.

In one embodiment, the water inventory information may include one or more of: fluid levels for one or more water tanks, capacity limits for each of the one or more water tanks, operational status for each of the one or more water tanks, and/or flow rates for one or more water flows. The one or more water flows may include one or more of: water flow rates to each of one or more processing units, recycled water flow rates from one or more distillation units, and/or recycled water flow rates from one or more stillage processing units, among others.

In one embodiment, the water inventory information may include inventory information for a plurality of water sources, including one or more of: one or more water sources and/or one or more recycled water sources; and the target water flow rates may include target flow rates for one or more of: water and/or recycled water, among others. The recycled water may include one or more of: fermentation broth recycle water, evaporator condensate recycle water, distillation bottoms recycle water, and/or treated water from an anaerobic digester, among others.

Biomass concentration may be expressed as % solids, % water, lb grain/lb water, or other weight or volume ratios or fractions thereof (e.g., fraction solids). In addition, % fermentable starch or weight fermentable starch/unit time or the same factors not limited to 'fermentable' starch may be used. For example, the raw grain may be analyzed to identify the fraction of starch or fermentable starch (excluding cellulosic, lignin and other generally non-fermentable starches). A more specific biomass rate or concentration (e.g., lb/hr fermentable starches or % fermentable sugars or fraction carbohydrates) may be multiplied by other described biomass concentration or rate factors such as % solids in the slurry stream, to calculate the % fermentable sugars in the slurry stream.

In one embodiment of the invention, biomass concentration information may include one or more of: feed rates for each mill, amp limits for each mill, water flow rates, and/or biomass concentration limit, among others.

In one embodiment of the invention, the biomass concentration information may be provided to the dynamic multivariate predictive model by another model with inputs comprising one or more of: measured temperature of the biomass, mill output, mill energy use, and/or water input to the fermentation feed. In this embodiment, at least a portion of the water input to the fermentation feed may be determined by indirect measurements related to the water input. The other model may also be a dynamic multivariate predictive model that includes time-response of biomass density to changes in one or more inputs to the biofuel production process. The one or more inputs to the biofuel production process may be dynamically filtered based on the time-response and provided as inputs to the other model, and one or more controllers for controlling biomass concentration may be configured in accordance with the time-response.

Execute the Model

In 815 of FIG. 8 the dynamic multivariate predictive model may be executed in accordance with the objective using the received water inventory and biomass concentration information as input, thereby generating model output comprising target values for a plurality of manipulated variables of the biofuel production process, including target water and/or biomass flow rates contributing to the fermentation feed in accordance with the objective.

In one embodiment, constraint information may be received as part of the objective. In this embodiment, the dynamic multivariate predictive model may be executed in accordance with the objective using the received water inventory, the one or more constraints, and biomass concentration information as input, thereby generating model output in accordance with the objective and subject to the one or more constraints.

In one embodiment, the constraint information may be equipment constraints. In this embodiment, executing the dynamic multivariate predictive model comprises executing the dynamic multivariate predictive model using the received water inventory and biomass concentration information, and the one or more equipment constraints as input, and wherein the target water and/or biomass flow rates are computed to approach and maintain the target feed rate for the fermentation feed subject to the one or more equipment constraints.

In one embodiment, executing the dynamic multivariate predictive model may include: determining a total water flow rate for the fermentation feed in accordance with the objective, and partitioning the total water flow rate for the fermentation feed among a plurality of water sources to determine respective target flow rates for each of the plurality of water sources.

Partitioning the total water flow rate for the fermentation feed among the plurality of water sources to determine respective target flow rates for each of the plurality of water sources may include performing the partitioning subject to one or more constraints regarding the plurality of water sources. The one or more constraints regarding the plurality of water sources may include one or more of: tankage constraints (including one or more of: limits on tank levels, limits on tank fill, and/or emptying rates), impurity constraints (including one or more of: percent impurity constraints and/or constraints on impurity type); and/or constraints on water transport. Constraints on water transport may include one or more of: operational status of one or more water transport elements and/or operational limits on one or more water transport elements.

As noted above, in some embodiments, the execution of the model may include executing the model in an iterative manner, e.g., via an optimizer, e.g., a nonlinear optimizer, varying manipulated variable values (e.g., mill feed rates, water flow, enzyme flow rates, etc.) and assessing the resulting model outputs and objective function, to determine values of the manipulated variables that satisfy the objective subject to one or more constraints, e.g., that optimize biomass concentration of the fermentation feed, subject to the constraints, thereby determining the target values for the manipulated variables.

Control the Process

In 820 of FIG. 8, the biofuel production process may be controlled, including water and/or biomass flow rates related to the fermentation feed of the biofuel production process, in accordance with the plurality of manipulated variables to stabilize water/biomass balance in the fermentation feed in accordance with the specified objective, including the specified target biomass concentration.

In one embodiment of the invention, executing the dynamic multivariate predictive model may include the dynamic multivariate predictive model determining a total water flow rate for the fermentation feed in accordance with the objective, and partitioning the total water flow rate for the fermentation feed among the plurality of water sources to determine respective target flow rates for each of the plurality of water sources. In this embodiment, executing the dynamic multivariate predictive model may also include controlling respective flow rates for each of the plurality of water sources in accordance with the respective target flow rates.

In one embodiment, controlling flow rates of water inventory and/or biomass concentration may include operating one or more flow controllers coupled to the dynamic multivariate model-based controller, where the one or more flow controllers may control one or more of: mill speed, pump speeds for one or more biomass feeds, and/or pump speeds for one or more water feeds. Controlling flow rates of water inventory may include controlling respective flow rates for each of a plurality of water sources in accordance with a respective target flow rate for each source.

Temperature Information and Temperature Control Constraints

In one embodiment of the invention, the dynamic multivariate predictive model specifies one or more temperature control constraints for the biofuel production process. The method for this embodiment may further include: receiving one or more temperature targets and a slurry throughput target for the fermentation feed, and receiving temperature information from the biofuel production process.

In this embodiment, executing the dynamic multivariate predictive model may include using the received water inventory and biomass concentration information and the temperature information as input, subject to the one or more temperature control constraints, to generate model output that may further include one or more target temperature values. In computing the model outputs, the dynamic multivariate predictive model may balance errors in the one or more temperature targets versus the slurry throughput target.

Controlling the flow rates of water inventory and/or biomass concentration may also include controlling temperatures related to the fermentation feed of the biofuel production process in accordance with the target temperature values to stabilize water/biomass and enzyme/biomass balance in the fermentation feed.

Temperature information from the biofuel production process may include one or more of: cook temperature, hydroheater temperature, cook flash temperature, and/or liquefaction temperature. The one or more target temperature values may include one or more of: a target cook temperature, a target hydroheater temperature, a target cook flash temperature, and/or a target liquefaction temperature.

Enzyme Flow Rates

In one embodiment of the invention, the dynamic multivariate predictive model may further specify relationships between biomass fractional flow rates and enzyme flow rates, and the method may further include: receiving enzyme flow rate information from the biofuel production process that may include one or more enzyme flow rates; executing the dynamic multivariate predictive model using the received water inventory and biomass concentration information, constraint information, and the enzyme flow rates as input, to generate target enzyme flow rates; and controlling enzyme flow rates related to the fermentation feed of the biofuel production process in accordance with the target enzyme flow rates to stabilize water/biomass and enzyme/biomass balance in the fermentation feed. In one embodiment of the invention, the enzyme flow rates may include respective ratios of enzyme addition rates to biomass addition rates. Controlling enzyme flow rates in accordance with the target enzyme flow rates may be performed to maintain the fermentation feed at a specified target feed rate.

In one embodiment of the invention, the dynamic multivariate predictive model may further specify at least one equipment setting as a capacity constraint, and controlling enzyme flow rates may include controlling enzyme ratios to increase milling and cooking capacity in the biofuel production process by increasing liquefaction agents to reduce slurry viscosity, or improve the break-down of the biomass, and allow higher flow rates within limits due to the at least one equipment setting. The at least one equipment setting may include at least one valve position, and the limits due to the at least one equipment setting may include line pressure limits and/or control valve ranges.

pH Relations in the Biofuel Production Process

In one embodiment of the invention, the dynamic multivariate predictive model specifies pH relationships in the biofuel production process. The method may further include: receiving pH information from the biofuel production process, and executing the dynamic multivariate predictive model may include using the received water inventory and biomass concentration information, and the pH information as input, and the model output may further include a target pH for the fermentation feed, and a pH control agent target. Controlling flow rates of water inventory and/or biomass concentration may further include controlling pH related to the fermentation feed of the biofuel production process in accordance with the target pH and pH control agent target.

The pH relations in the biofuel production process may include relations between pH and one or more of: mixing tank level of a pH control agent with slurry, ambient temperature, time of day, solids content of the fermentation feed, liquid temperature of the fermentation feed, and/or slurry flow rate of the fermentation feed. The pH information may include one or more of: the mixing tank level of the pH control agent with slurry, the ambient temperature, the time of day, the solids content of the fermentation feed, the liquid temperature of the fermentation feed, and/or the slurry flow rate of the fermentation feed.

Additional Embodiments

In some embodiments, a system for managing fermentation feed in a biofuel production process may include: a dynamic multivariate predictive model of biomass concentration and water inventory for a fermentation feed of the biofuel production process, and a dynamic multivariate predictive model-based controller coupled to the dynamic multivariate predictive model.

The dynamic multivariate predictive model may be executable: to receive water inventory and biomass information from the biofuel production process, to receive a specified objective for the fermentation feed specifying at least one targeted measurable attribute defining product quality for the fermentation feed, and to generate model output comprising target flow rates of water and/or biomass contributing to the fermentation feed in accordance with the specified objective.

The dynamic multivariate predictive model-based controller may be operable to control water flow rates and/or biomass concentration related to the fermentation feed of the biofuel production process in accordance with the target water and biomass flow rates to stabilize the water/biomass balance of the fermentation feed in accordance with the specified objective.

In one embodiment, a computer-accessible memory medium stores program instructions for a dynamic multivariate predictive model of biomass concentration and water inventory for a fermentation feed of the biofuel production process. In this embodiment, the program instructions may be executable to: receive a specified objective for a fermentation feed that specifies a target biomass concentration for the fermentation feed; receive process information that may include water inventory information and biomass concentration information from the biofuel production process; and execute the dynamic multivariate predictive model in accordance with the objective using the received water inventory and biomass concentration information as input, to generate model output comprising target values for a plurality of manipulated variables of the biofuel production process, including target water and/or biomass flow rates contributing to the fermentation feed in accordance with the objective.

In this embodiment, the program instructions may be further executable to: control the biofuel production process, including water and/or biomass flow rates related to the fermentation feed of the biofuel production process, in accordance with the plurality of manipulated variables to stabilize water/biomass balance in the fermentation feed in accordance with the specified objective, including the specified target biomass concentration.

Thus, various embodiments of the above model predictive control systems and methods may be used to manage a fermentation feed in a biofuel production process.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications. Note the section headings used herein are for organizational purposes only and are not meant to limit the description provided herein or the claims attached hereto.

We claim:

1. A computer-implemented method for managing fermentation feed in a biofuel production process, comprising:
providing a dynamic multivariate predictive model of biomass concentration and water inventory for a fermentation feed of the biofuel production process;
receiving a specified objective for the fermentation feed specifying a target biomass concentration and a target fermentation residual broth fraction for the fermentation feed;
receiving process information, comprising water inventory information and biomass concentration information, from the biofuel production process;
receiving constraint information specifying one or more constraints;
executing the dynamic multivariate predictive model in accordance with the objective using the received water inventory, the one or more constraints, and biomass concentration information as input, thereby generating model output comprising target values for a plurality of manipulated variables of the biofuel production process, including target water flow rates, target biomass flow rates, and target fermentation residual broth recycle rates; and
controlling the biofuel production process, including water flow rates, biomass flow rates, and fermentation residual broth recycle rates, in accordance with the target values for the plurality of manipulated variables.

2. The method of claim 1, wherein the dynamic multivariate predictive model specifies relationships between fermentation feed rates and equipment constraints; the constraint information further comprises one or more equipment constraints of the biofuel production process; the specified objective further comprises a target feed rate for the fermentation feed; and executing the dynamic multivariate predictive model further comprises generating target values of manipulated variables to approach and maintain the target feed rate for the fermentation feed subject to the one or more equipment constraints.

3. The method of claim 1, wherein the dynamic multivariate predictive model further specifies relationships between biomass fractional flow rates and enzyme flow rates; the process information further comprises enzyme flow rate information from the biofuel production process comprising one or more enzyme flow rates; executing the dynamic multivariate predictive model comprises executing the dynamic multivariate predictive model using the received water inventory and biomass concentration information, constraint information, and the enzyme flow rates as input; wherein the model output further comprises target enzyme flow rates; and wherein said controlling the biofuel production process further comprises controlling enzyme flow rates in accordance with the target enzyme flow rates.

4. The method of claim 3, wherein the enzyme flow rates comprise respective ratios of enzyme addition rates to biomass addition rates.

5. The method of claim 3, wherein said controlling enzyme flow rates in accordance with the target enzyme flow rates is performed to maintain the fermentation feed at a specified target feed rate.

6. The method of claim 5, wherein the dynamic multivariate predictive model further specifies at least one equipment setting as a capacity constraint, and wherein said controlling enzyme flow rates comprises controlling enzyme ratios to increase milling and cook capacity in the biofuel production process by increasing liquefaction agents to reduce slurry viscosity and allow higher flow rates within limits due to the at least one equipment setting.

7. The method of claim 6, wherein the at least one equipment setting comprises at least one valve position, and wherein the limits due to the at least one equipment setting comprise line pressure limits and/or control valve ranges.

8. The method of claim 1, wherein the dynamic multivariate predictive model comprises one or more of a linear model, a nonlinear model, a fundamental model, an empirical model, a neural network, a support vector machine, a statistical model, a rule-based model, or a fitted model.

9. The method of claim 1 wherein the objective further comprises one or more of: a target fermentation feed rate; a consistent water fraction of the fermentation feed; an operator specified objective; a predictive model specified objective; a programmable objective; a cost objective; a quality objective; an equipment maintenance objective; an equipment repair objective; an equipment replacement objective; an economic objective; a target throughput for the biofuel production process; an objective in response to emergency occurrences; a dynamic change in water inventory information; a dynamic change in biomass concentration information; and a dynamic change in one or more constraints on the biofuel production process.

10. The method of claim 1, wherein the objective for the fermentation feed is specified by one or more of a human operator and a program.

11. The method of claim 1, wherein the water inventory information includes one or more of: fluid levels for one or more water tanks; capacity limits for each of the one or more water tanks; operational status for each of the one or more water tanks; and flow rates for one or more water flows.

12. The method of claim 11, wherein the one or more water flows comprise one or more of: water flow rates to each of one or more processing units; recycled water flow rates from one or more distillation units; and recycled water flow rates from one or more stillage processing units.

13. The method of claim 1, wherein the water inventory information comprises inventory information for a plurality of water sources, comprising one or more of: one or more water sources; and/or one or more recycled water sources; and wherein the target water flow rates comprise target flow rates for one or more of: water and recycled water.

14. The method of claim 13, wherein the recycled water comprises one or more of: fermentation broth recycle water; evaporator condensate recycle water; distillation bottoms recycle water; and treated water from an anaerobic digester.

15. The method of claim 13, wherein said executing the dynamic multivariate predictive model comprises the dynamic multivariate predictive model: determining a total water flow rate for the fermentation feed in accordance with the specified objective; and partitioning the total water flow rate for the fermentation feed among the plurality of water sources to determine respective target flow rates for each of the plurality of water sources; and wherein said controlling flow rates of water inventory comprises controlling respective flow rates for each of the plurality of water sources in accordance with the respective target flow rates.

16. The method of claim 15, wherein said partitioning the total water flow rate for the fermentation feed among the plurality of water sources to determine respective target flow rates for each of the plurality of water sources comprises performing said partitioning subject to one or more constraints regarding the plurality of water sources.

17. The method of claim 16, wherein the one or more constraints regarding the plurality of water sources comprise one or more of: limits on tank levels; limits on tank fill or emptying rates; percent impurity constraints; constraints on impurity type; and constraints on water transport.

18. The method of claim 17, wherein the constraints on water transport comprise one or more of: operational status of one or more water transport elements; and operational limits on one or more water transport elements.

19. The method of claim 1, wherein said biomass concentration information comprises one or more of: feed rates for each mill, amp limits for each mill, water flow rates, stream density, temperature and/or biomass concentration limit.

20. The method of claim 1, wherein the biomass concentration information is provided by another model with inputs comprising one or more of: measured temperature of the biomass; mill output; mill energy use; and water input to the fermentation feed.

21. The method of claim 20, wherein at least a portion of the water input to the fermentation feed is determined by indirect measurements related to the water input.

22. The method of claim 20, wherein the other model is a dynamic multivariate predictive model that includes time-response of biomass density to changes in one or more inputs to the biofuel production process.

23. The method of claim 20, wherein the one or more inputs to the biofuel production process are dynamically filtered based on the time-response and provided as inputs to the other model, and wherein one or more controllers for controlling biomass concentration are configured in accordance with the time-response.

24. The method of claim 1, wherein the one or more constraints comprise one or more of: mill amperage limit that limits fermentation feed rate and/or cook flow rate; thin stillage tank level limits that limit fermentation residual broth recycle rate; slurry water tank level limits that limit water addition rates; pressure limits that limit pump capabilities, safety or processing rates; back-end processing rate limits that limit fermentation fill rate; and/or cook temperature limits that limit fermentation fill rate; water constraints; biomass constraints; feed constraints; equipment constraints; capacity constraints; temperature constraints; pressure constraints; energy constraints; market constraints; economic constraints; or operator imposed constraints.

25. The method of claim 24, wherein the operator constraints comprise one or more of operating limits for pumps; operational status of pumps; tank capacities; operating limits for tank pressures; operational status of tanks; operating limits for valve pressures; operating limits for valve temperatures; and operating limits for pipe pressures.

26. The method of claim 1, wherein said constraint information comprises dynamic constraint information.

27. The method of claim 1, wherein said executing the dynamic multivariate predictive model in accordance with the objective comprises: an optimizer executing the dynamic multivariate predictive model in an iterative manner to determine target values for the plurality of manipulated variables that satisfy the specified objective subject to one or more constraints.

28. The method of claim 1, wherein said controlling flow rates of water inventory and/or biomass concentration comprises: operating one or more flow controllers coupled to the dynamic multivariate predictive model, wherein the one or more flow controllers control one or more of: mill speed; pump speeds for one or more biomass feeds; and pump speeds for one or more water feeds.

29. A system for managing fermentation feed in a biofuel production process, comprising:
   a dynamic multivariate predictive model of biomass concentration and water inventory for a fermentation feed of the biofuel production process
   a dynamic multivariate predictive model-based controller coupled to the dynamic multivariate predictive model; and program instructions that, when executed, cause controller to:
  receive process information, comprising water inventory and biomass information, from the biofuel production process;
  receive a specified objective for the fermentation feed specifying a target biomass concentration and a target fermentation residual broth fraction for the fermentation feed;
  receive constraint information specifying one or more constraints
  execute the dynamic multivariate predictive model, in accordance with the objective using the received water inventory, the one or more constraints, and biomass concentration information as input, thereby generating model output comprising target values for a plurality of manipulated variables of the biofuel production process, including target flow rates of water and biomass, and target fermentation residual broth recycle rates; and
  control the biofuel production process, including water flow rates, biomass flow rates, and fermentation residual broth recycle rates in accordance with the target values for the plurality of manipulated variables.

30. A non-transitory computer-accessible memory medium for use in managing fermentation feed in a biofuel production process, comprising:

a dynamic multivariate predictive model of biomass concentration and water inventory for a fermentation feed of the biofuel production process; and
program instructions that, when executed, cause a controller to:
  receive process information, comprising water inventory and biomass information, from the biofuel production process;
  receive a specified objective for the fermentation feed specifying a target biomass concentration and a target fermentation residual broth fraction for the fermentation feed;
  receive constraint information specifying one or more constraints;
  execute the dynamic multivariate predictive model in accordance with the objective using the received water inventory, the one or more constraints, and biomass concentration information as input, thereby generating model output comprising target values for a plurality of manipulated variables of the biofuel production process, including target flow rates of water and biomass, and target fermentation residual broth recycle rates; and
  control the biofuel production process, including water flow rates, biomass flow rates, and fermentation residual broth recycle rates in accordance with the target values for the plurality of manipulated variables.

* * * * *